United States Patent [19]

Meijer

[11] Patent Number: 4,678,817

[45] Date of Patent: Jul. 7, 1987

[54] NOVEL DESENSITIZED KETONE PEROXIDE COMPOSITIONS AND THEIR USE IN THE MANUFACTURE OF FOUNDRY CORES OR MOULDS

[75] Inventor: John Meijer, Deventer, Netherlands

[73] Assignee: Akzo NV, Arnhem, Netherlands

[21] Appl. No.: 883,705

[22] Filed: Jul. 9, 1986

[30] Foreign Application Priority Data

Jul. 16, 1985 [NL] Netherlands .................. 8502042

[51] Int. Cl.$^4$ ................... B22C 11/22; C01B 15/00
[52] U.S. Cl. ............................ 523/144; 523/145; 523/146; 252/186.26; 164/527
[58] Field of Search ............... 523/144, 145, 146, 143; 252/186.26; 164/527

[56] References Cited

U.S. PATENT DOCUMENTS

| | | | |
|---|---|---|---|
| T998,005 | 9/1980 | Orwoll et al. | 252/186.26 |
| 3,538,011 | 11/1970 | van der Klaauw | 252/186.26 |
| 4,268,425 | 5/1981 | Gardikes | 523/143 |
| 4,436,844 | 3/1984 | Schroeder et al. | 523/146 |
| 4,602,069 | 7/1986 | Dunnavant et al. | 523/141 |

*Primary Examiner*—Lewis T. Jacobs
*Attorney, Agent, or Firm*—Parkhurst & Oliff

[57] ABSTRACT

This disclosure relates to novel desensitized ketone peroxide compositions containing as desensitizing agent 2,2,4-trimethyl-1,3-pentanediol diisobutyrate. It further relates to the use of these compositions in the manufacture of foundry cores or moulds.

5 Claims, No Drawings

NOVEL DESENSITIZED KETONE PEROXIDE COMPOSITIONS AND THEIR USE IN THE MANUFACTURE OF FOUNDRY CORES OR MOULDS

The invention relates to a desensitized ketone peroxide composition which contains a monocarboxylic acid diester of an alkane diol as desensitizing agent.

Ketone peroxide compositions of the type indicated above are disclosed in U.S. Pat. No. 3 649 546, which mentions various desensitizing esters, including monoesters and diesters. According to said patent specification only those esters are effective desensitizing agents that fall within the composition range where the sum of the carbon and oxygen atoms is from 9 to 16 in the boiling range of 140° to 250° C., and preferably from 9 to 14 in the boiling range of 170° to 218° C. Esters that fall outside these boiling ranges, such as ethyl benzoxyacetate (boiling point 265° C.), dimethyl phthalate (boiling point 282° C.) and glycerol diacetate (boiling point 280° C.), do not meet the safety standards set for a desensitizing agent in said patent specification.

The invention relates to a desensitized ketone peroxide composition of the type indicated above, characterized in that the diester consists of 2,2,4-trimethyl-1,3-pentanediol diisobutyrate.

The sum of the carbon and oxygen atoms of 2,2,4-trimethyl-1,3-pentanediol diisobutyrate is 19 and the boiling point is 280° C. contrary to what was to be expected in view of U.S. Pat. No. 3 649 546, it has been found that the present ester is virtually a just as effective desensitizing agent as the carboxylic diesters recommended in said patent specification and derived from an alkane diol, such as propylene glycol diacetate.

Moreover, it has been found that the composition according to the invention can very satisfactorily be used in the manufacture of foundry cores or moulds.

The present ketone peroxide composition may contain any ketone peroxide desired.

As examples thereof may be mentioned acetone peroxide, methyl ethyl ketone peroxide, diethyl ketone peroxide, methyl propyl ketone peroxide, methyl isobutyl ketone peroxide and alicyclic ketone peroxides such as cyclopentanone peroxide, cyclohexanone peroxide, methylcyclohexanone peroxide and trimethyl cyclohexanone peroxide. It is preferred that use should be made of methyl ethyl ketone peroxide.

2,2,4-Trimethyl-1,3-pentanediol diisobutyrate may be prepared by esterification in a known manner of 2,2,4-trimethyl-1,3-pentanediol with isobutyric acid. This compound is also commercially available as a colourless liquid.

The present ketone peroxide composition may also contain other components, such as sequestering agents, antioxidants and organic solvents.

The ketone peroxide compositions may be prepared in the usual manner by having the ketone react with $H_2O_2$ under the influence of $H_2SO_4$ in the presence of the desensitizing agent. After neutralization and separation of the aqueous phase the composition is dried. If necessary, some additional amount of ester may still be added to the composition. Generally, the composition contains 10–75% by weight of ketone peroxide, 10–85% by weight of desensitizing agent and up to 10% of water. For practical purposes the active oxygen content of the composition is generally in the range of 3 to 11%, preferably 6 to 9%.

The present ketone peroxide compositions may find application in many fields, such as the polymerization of vinyl ester resins and unsaturated polyester resins and the manufacture of foundry cores and moulds.

It is preferred that the ketone peroxide composition should be applied in the manufacture of foundry cores or moulds, which is described, among other places, in European Patent Application EP No. 0 084 689. In the process described in it a mixture of a granular filler and a synthetic resin is cured with a ketone peroxide in a core or mould box, the important criteria being the initial and the final degrees of curing, which are determined by measuring the flexural strength of the foundry core or mould immediately after removal from the core or mould box and after a considerable time has lapsed.

It should be added that for this use EP No. 0 084 689 discloses diesters derived from aliphatic dicarboxylic acids, but does not mention esters of the present type. As compared with said diesters derived from dicarboxylic acids, the cost price of 2,2,4-trimethyl-1,3-pentanediol diisobutyrate is considerably lower, and its effectiveness in the manufacture of foundry moulds or cores is equivalent.

The present invention will be further described in the following examples.

EXAMPLE 1

Into a three-necked flask there were charged, with stirring, methyl ethyl ketone (1 mole), 2,2,4-trimethyl-1,3-pentanediol diisobutyrate (100 g) and sulphuric acid (30 m. equiv. H+, added as 50%-$H_2SO_4$ solution in water). Subsequently, hydrogen peroxide (1,6 moles, added as 70%-$H_2O_2$ solution in water) was added to the stirred reaction mixture dropwise, the temperature being kept at about 30° C. by cooling. After continued stirring for 1 hour at 30° C. the mixture was neutralized to a pH of 5,5 to 6,5 by adding a 4N KOH solution in water. After separation of the aqueous phase from the organic phase, the latter phase was dried by distillation under reduced pressure in a rotating vacuum evaporator.

The methyl ethyl ketone conversion was 70%, the amount of water 2%, and the amount of active oxygen 10%.

To the formulation was added 2,2,4-trimethyl-1,3-pentanediol diisobutyrate in an amount such that the resulting active oxygen content was 9%. The resulting formulation was subjected to a so-called PVT safety test. This test is described in: Vervoer gevaarlijke stoffen, Dec. 23, 1980, Aanhangsel Al bij bijlage A, p.p. 907, 908, 915: Staatsuitgeverij. In this test (see also Example 2 of U.S. Pat. No. 3 649 546) 10 g of the material to be tested is heated with a standardized gas flame in a pressure vessel fitted with a burst diaphragm calibrated for 6 bar. In the side wall of the pressure vessel is a blowoff aperture having an adjustable diameter. The test procedure consists in that the smallest aperture that can be tolerated without rupture of the burst diaphragm is determined for the peroxide upon its decomposition (explosure, combustion). The smaller the aperture, the less hazardous the formulation. The result is given in Table 1.

EXAMPLE 2

Use being made of the same procedure as described in Example 1, methyl ethyl ketone peroxide was prepared in the presence of 2,2,4-trimethyl-1,3-pentanediol diisobutyrate as desensitizing agent and 10 m.equiv. H+ and 1,7 moles $H_2O_2$. The methyl ethyl ketone conversion was 68%, the amount of water 2% and the amount of active oxygen 9,98%. Further, 2,2,4-trimethyl-1,3-pentanediol diisobutyrate was added in an amount such that the resulting active oxygen content was 9%, after which a PVT safety test was carried out. For the result see Table 1.

COMPARATIVE EXAMPLE 1

Use being made of the same procedure as described in Example 1, methyl ethyl ketone peroxide was prepared in the presence of propylene glycol diacetate as desensitizing agent. The methyl ethyl ketone conversion was 72%, the amount of water 0,83% and the amount of active oxygen 11,92%. Propylene glycol diacetate was added in such an amount as resulted in an active oxygen content of 9%. Subsequently, a PVT safety test was carried out. The result is given in Table 1.

TABLE 1

| | PVT test results |
|---|---|
| Formulation | PVT test Diameter of blowoff aperture (mm) |
| Example 1 | 3,0 |
| Example 2 | 3,0 |
| Comparative Example 1 | 2,0 |

Table 1 shows that 2,2,4-trimethyl-1,3-pentanediol diisobutyrate is practically a just as effective desensitizing agent as the prior art propylene glycol diacetate.

EXAMPLE 3

The methyl ethyl ketone peroxide composition of Example 1 was used for making a foundry core. To this end 2,2,4-trimethyl-1,3-pentanediol diisobutyrate was added to said composition in such an amount as resulted in an active oxygen content of 8%.

The dimensions of the foundry core to be made were 2,2 cm×2,2 cm×1,7 cm. In a core sand mixer of the PKM type (supplied by Georg Fisher) 3000 parts of sand (55 AFA, supplied by Sigrano) and a mixture of 36 parts of furan resin (Hardox ® 80, supplied by Sapic) and 0,108 parts of γ-aminopropyl triethoxysilane (Silane 1100, supplied by Union Carbide) were intermixed over a period of 2 minutes. Subsequently, 10,8 parts of the methyl ethyl ketone peroxide composition were added, followed by mixing for another 1,5 minutes. Next, the composition was placed in a core box, compacted and the excess sand mixture scraped off. In a following step the core box was placed in a gassing apparatus by which, at room temperature and for 1 second, $SO_2$ was forced through it at a pressure of 2-2,5 bar. Following this operation the core was flushed for 12 seconds with air at a pressure of about 1,5 bar, after which the core was removed from the box. The flexural strength of the core was measured twice, viz. 13 seconds and 24 hours after termination of the gassing operation and in accordance with the method described in DIN No. 52404. The results are given in Table 2.

EXAMPLE 4

A foundry core was made in accordance with the procedure described in Example 3, use being made however of 14,4 parts of methyl ethyl ketone composition containing 8% of active oxygen. The results are given in Table 2.

COMPARATIVE EXAMPLES 2 AND 3

Foundry cores were made in the way indicated in Example 3, except that use was made of respectively 10,8 parts (Comparative Experiment 2) and 14,4 parts (Comparative Experiment 3) of the ketone peroxide composition of Comparative Example 1, to which propylene glycol diacetate was added in such an amount as resulted in an active oxygen content of 8%. The results are listed in Table 2.

TABLE 2

| | Initial and final curing results | | |
|---|---|---|---|
| | | Flexural strength foundry core in $N/cm^2$ | |
| Desensitizing agent | % formulation based on resin | after 13 sec. | after 24 hours |
| 2,2,4-trimethyl-1,3-pentanediol diisobutyrate | | | |
| Example 3 | 30 | 175 | 540 |
| Example 4 | 40 | 180 | 570 |
| propylene glycol diacetate | | | |
| Comparative Example 2 | 30 | 60 | 345 |
| Comparative Example 3 | 40 | 115 | 390 |

Table 2 shows that use of the present ester leads to considerably better curing results than are obtained with propylene glycol diacetate.

I claim:

1. A desensitized ketone peroxide composition which contains as desensitizing agent a monocarboxylic acid diester of an alkane diol, characterized in that the diester consists of 2,2,4-trimethyl-1,3-pentanediol diisobutyrate.

2. A desensitized ketone peroxide composition according to claim 1, characterized in that the ketone peroxide is methyl ethyl ketone peroxide.

3. A desensitized ketone peroxide composition according to claim 1, characterized in that the composition contains 10-85% by weight of 2,2,4-trimethyl-1,3-pentanediol diisobutyrate and the active oxygen content of the composition is in the range of 3-11%.

4. A process for the manufacture of a foundry core or mould, in which process a composition comprising a granular filler, a synthetic resin which is curable under the influence of an acid and a desensitized ketone peroxide composition is formed into the desired foundry core or mould and treated with sulphur dioxide, characterized in that the ketone peroxide composition contains 2,2,4-trimethyl-1,3-pentanediol diisobutyrate as desensitizing agent.

5. A process according to claim 4, characterized in that the ketone peroxide is methyl ethyl ketone peroxide.

* * * * *

UNITED STATES PATENT AND TRADEMARK OFFICE
CERTIFICATE OF CORRECTION

PATENT NO. : 4,678,817
DATED : July 7, 1987
INVENTOR(S) : John MEIJER

It is certified that error appears in the above-identified patent and that said Letters Patent is hereby corrected as shown below:

Column 1, line 11, change "3 649 546," to --3,649,546--;
          line 31, change "3 649 546," to --3,649,546--.

Column 2, line 32, change "(1,6" to --(1.6--;
          line 37, change "5,5 to 6,5" to --5.5 to 6.5--;
          line 52, change "3 649 546)" to --3,649,546)--.

Column 3, line 1, change "1,7" to --1.7--;
          line 3, change "9,98%." to --9.98%.--;
          line 15, change "0,83%" to --0.83%--;
          line 16, change "11,92%." to --11.92%.--;
          line 26, change "3,0" to --3.0--;
          line 27, change "3,0" to --3.0--;
          line 28, change "2,0" to --2.0--;
          line 41, change "2,2 cm X 2,2 cm X 1,7" to --2.2 cm X 2.2 cm X 1.7--;
          line 45, change "0,108" to --0.108--;
          line 47, change "10,8" to --10.8--;
          line 49, change "1,5" to --1.5--;
          line 54, change "2-2,5" to --2-2.5--;
          line 56, change "1,5" to --1.5--.

UNITED STATES PATENT AND TRADEMARK OFFICE
CERTIFICATE OF CORRECTION

PATENT NO. : 4,678,817
DATED : July 7, 1987
INVENTOR(S) : John Meijer

It is certified that error appears in the above-identified patent and that said Letters Patent is hereby corrected as shown below:

Column 4, line 5, change "14,4" to --14.4--;
line 12, change "10,8" to --10.8--;
change "14,4" to --14.4--.

Signed and Sealed this

Eighth Day of December, 1987

Attest:

DONALD J. QUIGG

*Attesting Officer*   *Commissioner of Patents and Trademarks*